United States Patent
Gatto et al.

(10) Patent No.: US 7,960,321 B2
(45) Date of Patent: *Jun. 14, 2011

(54) OIL-SOLUBLE MOLYBDENUM DERIVATIVES DERIVED FROM HYDROXYETHYL-SUBSTITUTED MANNICH BASES

(75) Inventors: Vincent J. Gatto, Baton Rouge, LA (US); John T. Loper, Richmond, VA (US); Gregory P. Liesen, Mechanicsville, VA (US)

(73) Assignee: Afton Chemical Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/121,462

(22) Filed: May 15, 2008

(65) Prior Publication Data
US 2009/0075849 A1    Mar. 19, 2009

Related U.S. Application Data

(62) Division of application No. 10/970,743, filed on Oct. 20, 2004, now Pat. No. 7,884,059.

(51) Int. Cl.
*C10M 159/18* (2006.01)
*C07F 11/00* (2006.01)

(52) U.S. Cl. ............... 508/362; 508/542; 556/57

(58) Field of Classification Search .......... 508/362, 508/108, 542, 572; 556/57
See application file for complete search history.

(56) References Cited

U.S. PATENT DOCUMENTS

| | | | |
|---|---|---|---|
| 4,164,473 A | 8/1979 | Coupland et al. | |
| 4,259,195 A | 3/1981 | King et al. | |
| 4,261,843 A | 4/1981 | King et al. | |
| 4,266,945 A | 5/1981 | Karn | |
| 4,360,438 A | 11/1982 | Rowan et al. | |
| 4,501,678 A | 2/1985 | Katayama et al. | |
| 4,529,526 A | 7/1985 | Inoue et al. | |
| 4,647,293 A | 3/1987 | Cahill et al. | |
| 4,692,256 A | 9/1987 | Umemura et al. | |
| 4,705,641 A | 11/1987 | Goldblatt et al. | |
| 4,812,246 A | 3/1989 | Yabe | |
| 4,832,867 A | 5/1989 | Seiki et al. | |
| 5,458,807 A | 10/1995 | Tamoto | |
| 5,512,067 A | 4/1996 | Loper | |

(Continued)

FOREIGN PATENT DOCUMENTS
EP    0 049 094    4/1982
(Continued)

OTHER PUBLICATIONS

Tadeusz G. et al, "New insights into the chemistry of oxomolybdenum (VI) complexes with N-salicylidene-2-aminoethanol", STN File CA Abstract Accession No. 140:156124, Inorganica Chimica Acta (2003), 356, 387-392.

(Continued)

*Primary Examiner* — Glenn A Caldarola
*Assistant Examiner* — Vishal Vasisth
(74) *Attorney, Agent, or Firm* — Luedeka, Neely & Graham, P.C.

(57) ABSTRACT

The present disclosure relates to organic molybdenum complexes prepared by reacting a Mannich base with a source of molybdenum. The complexes may be useful in lubricating oil compositions as at least one of an antioxidant, a deposit control additive, and a friction modifier. The organic molybdenum complexes may show a reduced tendency to color finished oils.

30 Claims, 2 Drawing Sheets

U.S. PATENT DOCUMENTS

| | | | |
|---|---|---|---|
| 5,605,880 | A | 2/1997 | Arai et al. |
| 5,650,381 | A | 7/1997 | Gatto et al. |
| 5,658,862 | A | 8/1997 | Vrahopoulou |
| 5,665,684 | A | 9/1997 | Arai et al. |
| 5,688,748 | A | 11/1997 | Tomizawa |
| 5,696,065 | A | 12/1997 | Tanaka et al. |
| 5,736,491 | A | 4/1998 | Patel et al. |
| 5,786,307 | A | 7/1998 | Igarashi et al. |
| 5,807,813 | A | 9/1998 | Yamada |
| 5,814,587 | A | 9/1998 | Vrahopoulou et al. |
| 5,837,657 | A | 11/1998 | Fang et al. |
| 5,840,672 | A | 11/1998 | Gatto |
| 5,880,073 | A | 3/1999 | Tomizawa et al. |
| 6,103,674 | A | 8/2000 | Nalskik et al. |
| 6,174,842 | B1 | 1/2001 | Gatto et al. |
| RE37,363 | E | 9/2001 | Gatto et al. |
| 6,362,355 | B1 | 3/2002 | Steckel et al. |
| 6,528,463 | B1 | 3/2003 | Gatto et al. |
| 6,566,311 | B1 | 5/2003 | Nalesnik |
| 6,599,865 | B1 | 7/2003 | Esche, Jr. et al. |
| 6,645,921 | B2 | 11/2003 | Gatto |
| 2003/0171226 | A1* | 9/2003 | Gatto .................... 508/362 |
| 2003/0224949 | A1 | 12/2003 | Ruhe, Jr. et al. |
| 2004/0198615 | A1 | 10/2004 | Friend et al. |

FOREIGN PATENT DOCUMENTS

| | | |
|---|---|---|
| EP | 0 447 916 | 6/1994 |
| EP | 0 768 366 | 6/2001 |
| EP | 1 371 716 A1 | 12/2003 |
| GB | 2 053 265 A | 2/1981 |
| GB | 2 053 266 A | 2/1981 |
| GB | 2 053 267 A | 2/1981 |
| GB | 2 053 268 A | 2/1981 |
| GB | 2 064 548 A | 6/1981 |
| JP | 51148707 | 12/1976 |
| WO | WO 95/07962 | 3/1995 |
| WO | WO 95/07963 | 3/1995 |
| WO | WO 95/07964 | 3/1995 |
| WO | WO 95/07966 | 3/1995 |
| WO | WO 95/27022 | 10/1995 |

OTHER PUBLICATIONS

Hu, Rui-Xiang et al., "Synthesis, spectroscopic studies and crystal structure of molybdenum (VI) Schiff-base complexes", STN File CA Abstract Accession No. 135:235348, Huaxue. Xuebao (2001), 59 (6), 972-975.

Derwent Abstract Accession No. 78939C/45, BE 884 007 A (Chevron Research Co) Oct. 16, 1980.

Derwent Abstract Accession No. 78937C/45, BE 884 007 A (Chevron Research Co) Oct. 16, 1980.

Winfried Plass, "Synthesis, Structure and Oxygen Atom Transfer Reactions for Dioxomolybdenum(VI) Complexes with Multidentate Amine Alcohols", Z. anorg. allg. Chem. 623, 1997, pp. 997-1005.

* cited by examiner

OIL-SOLUBLE MOLYBDENUM DERIVATIVES DERIVED FROM HYDROXYETHYL-SUBSTITUTED MANNICH BASES

RELATED APPLICATION

This application is a divisional of U.S. patent application. Ser. No. 10/970,743 now U.S. Pat. No. 7,884,059, filed Oct. 20, 2004, which is incorporated herein by reference in its entirety.

FIELD OF THE INVENTION

This application relates to an organic molybdenum complex and a process for making the organic molybdenum complex. The complex may be useful as an antioxidant, a deposit control additive, an anti-wear additive, and a friction modifier in, e.g., lubricant compositions.

BACKGROUND OF THE INVENTION

Lubricating oils for internal combustion engines of automobiles or trucks are subjected to a demanding environment during use. This environment results in the oil suffering from oxidation. The oxidation is catalyzed by the presence of impurities in the oil, such as iron compounds. Oxidation is also promoted by the elevated temperatures of the oil during use. This oxidation of lubricating oils during use is typically controlled, at least to some extent, by the use of antioxidant additives that may extend the useful life of the oil, for example by reducing or preventing unacceptable viscosity increases.

There have been a number of attempts to employ lubricants to reduce the friction in an internal combustion engine so as to reduce the fuel consumption of the engine. Numerous classes of lubricant additives have been suggested for use as friction modifiers and to increase the energy efficiency imparted to an engine by a lubricant.

Molybdenum containing additives are known to deliver a variety of beneficial properties to lubricants. Non-limiting examples of lubricants that benefit from the addition of molybdenum include passenger car motor oils, natural gas engine oils, heavy-duty diesel oils, and railroad oils. Over the years molybdenum, when used properly, has been shown to deliver improved anti-wear protection, improved oxidation control, improved deposit control, and improved friction modification for fuel economy.

U.S. Pat. No. 4,692,256 discloses a molybdenum-containing lubricant composition comprising a sulfur compound and an oil-soluble molybdenum compound. The oil-soluble molybdenum compound is prepared by reacting a hexavalent molybdenum compound with an alkyl amine.

U.S. Pat. No. 4,259,195 is directed to antioxidant additives for lubricating oils. The additives are prepared by combining a polar promoter, an acidic molybdenum compound, and a basic nitrogen compound to form a molybdenum-containing composition.

U.S. Pat. No. 4,266,945 discloses molybdenum-containing compositions prepared by the reaction of a molybdenum acid with a phenol, or an aldehyde condensation product of the phenol, and a primary or secondary amine.

The performance of molybdenum compounds as friction modifiers may be determined by a number of factors, including but not limited to:
1. The system in which the additive is being tested. The design of the bench test, rig test, or engine test by which the molybdenum additive is being evaluated affects performance.
2. The other types of additives present in the oil. It is well-known that molybdenum additives exhibit synergistic responses with additives such as sulfurized antioxidants and EP additives, ZDDP, and alkylated diphenylamines.
3. The chemical structure of the oil-soluble molybdenum compound. It is well-known that structurally different molybdenum additives respond differently as friction modifiers under a given set of test conditions.

Existing molybdenum technology, however, suffers from a number of problems that have limited its widespread use in lubricants. These problems include at least one of color, oil solubility, cost and corrosion.

Color Imparted by Molybdenum Compounds

Many molybdenum technologies deliver high levels of color when used even at moderate levels in crankcase oils. The tendency of molybdenum additives to color finished crankcase oils has resulted in the commercialization of a limited number of oil soluble molybdenum products. The contribution of molybdenum additives to finished oil color is purely an aesthetic issue, and is unrelated to any performance property or product compatibility of the molybdenum additives. However, in certain lubricants, a light oil is viewed as a clean oil. Alternatively, a dark oil may sometimes be viewed as a used oil. From a marketing standpoint, it may be undesirable for the consumer to perceive that a specific motor oil brand contains used oil since used oil represents low performance. Light oils may therefore be desired for marketing purposes.

When highly colored molybdenum sources are used at low levels, e.g. 100-150 ppm-delivered molybdenum as is typically required for oxidation, deposit and wear control, discoloration is not substantial but may still be visible. However, when these highly colored molybdenum compounds are used at high levels, e.g. 400-1000 ppm-delivered molybdenum as is generally required for friction modification, discoloration is often significant.

Traditionally, the color of fully formulated crankcase oils has been determined using the ASTM 0 1500 color scale. Two types of unacceptable colors are possible. The first type of discoloration results in a dark rating on the D 1500 scale. The amount of acceptable finished lubricant darkening depends on the customer and application. There are no set standards for the amount of discoloration or darkening that is allowed. Generally, D 1500 ratings equal to or greater than 5.0 are considered unacceptable for a finished crankcase oil. Certain customers may find it difficult to market and sell such dark crankcase oils. The second type of discoloration produces "no match" on the D 1500 color scale. These finished crankcase oils, in addition to showing no match, are also very dark. Again, certain customers may find it difficult to market and sell such dark crankcase oils.

Oil Solubility of Molybdenum Compounds

Many commercially available molybdenum additives designed for use in lubricants exhibit limited solubility in the finished lubricant product. For widespread use of a molybdenum product in lubricant applications, the product will generally not only be soluble at friction modifier treat-levels in the finished lubricant, it will generally also be soluble in the additive concentrates used to prepare the finished lubricant. An acceptable degree of solubility has been difficult to obtain in the past.

Cost of Molybdenum Compounds

Molybdenum has long been viewed as an expensive additive for crankcase applications. Part of the reason for the high cost stems from the fact that many of the commercial molybdenum products have low levels, e.g. less than 5% by weight, of molybdenum in the additive. In some cases, expensive organic ligands or expensive manufacturing processes are used to produce the commercial molybdenum compounds. There is a need for products with higher molybdenum, contents prepared from lower cost raw materials.

Corrosive Effects of Certain Molybdenum Compounds

Many molybdenum technologies contain sulfur. The presence of sulfur in various crankcase applications may be detrimental because certain types of sulfur are incompatible with elastomer seals, and may be corrosive. Even the less aggressive forms of sulfur can be corrosive in very high temperature crankcase environments where significant amounts of oxygen and water are present. There are also trends to reduce the amount of sulfur present in finished crankcase lubricants. As these trends start to become a reality, additives containing sulfur will become less desirable.

It is also well-known that certain molybdenum-containing friction modifiers function by a decomposition mechanism that results in the formation of a mixed molybdenum sulfide/molybdenum oxide layer on the metal surface of the engine. The molybdenum species that form on the metal surface may vary significantly, and their composition is affected by the types of additives in the lubricant and the engine or test design. For example, it is known that molybdenum dithiocarbamates decompose when heated to produce products that include free amine and carbon disulfide. Both such products are aggressive towards any copper that may be present in the engine bearings. Furthermore, free amines are known to be aggressive towards certain types of elastomer seals present in a wide variety of engines. It is therefore desirable from a compatibility standpoint to develop new additives that are low in sulfur and free amines.

It has unexpectedly been found that the molybdenum additives of the present invention may provide benefits to compositions, including lubricating compositions, without the problems commonly associated with molybdenum additives. The properties of the organic molybdenum complexes disclosed herein may include at least one of improved effectiveness as friction modifiers, reduced tendency to color finished crankcase oils, low cost of raw materials, and a simplified production process.

SUMMARY OF THE INVENTION

In accordance with the present disclosure, there is provided an organic molybdenum complex comprising the reaction product of (i) an optionally substituted hydroxyaromatic compound; (ii) an aldehyde source; (iii) an N-hydroxyethyl substituted diamine; and (iv) a molybdenum source.

According to another aspect of the present disclosure, there is provided a process for preparing an organic molybdenum complex, comprising (a) reacting an optionally substituted hydroxyaromatic compound with an aldehyde source and an N-hydroxyethyl substituted diamine to yield a Mannich base; and (b) reacting the Mannich base with a molybdenum source to form the organic molybdenum complex.

According to yet another aspect of the present disclosure, there is provided a lubricating oil composition comprising a major amount of an oil of lubricating viscosity and an organic molybdenum complex prepared by a process comprising (a) reacting an optionally substituted hydroxyaromatic compound with an aldehyde source and an N-hydroxyethyl substituted diamine to yield a Mannich base; and (b) reacting the Mannich base with a molybdenum source to form the organic molybdenum complex.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DESCRIPTION OF THE EMBODIMENTS

Reference will now be made in detail to the present embodiments of the disclosure, illustrations of which are illustrated in the accompanying drawings.

The present disclosure relates to an oil-soluble molybdenum composition useful as an antioxidant, a deposit control additive, and a friction modifier. The composition comprises an organic molybdenum complex prepared by a two-step process. First, a Mannich base is prepared by reacting, in an organic solvent such as toluene, an alkylated phenol, an aldehyde source, and an N-hydroxyethyl substituted diamine. The Mannich base thus formed is then reacted with a molybdenum source, such as molybdenum trioxide, and water, with the azeotropic removal of water, to form the organic molybdenum complex. One advantage of the organic molybdenum complex prepared by this process is that the complex may show a reduced tendency to color finished oils, and may show improved performance as a friction modifier for fuel economy applications.

I. Preparation of the Mannich Base

Mannich bases may be obtained by reacting a hydroxyaromatic compound, an aldehyde source, and an N-hydroxyethyl substituted diamine. According to certain aspects of the present disclosure, the Mannich base may be prepared by reacting an alkylated phenol with an aldehyde source and an N-hydroxylethyl-substituted diamine in toluene with azeotropic removal of water.

Any hydroxyaromatic compound may be used provided it reacts with the aldehyde source and the N-hydroxyethyl-substituted diamine, and further provided that the final product shows sufficient oil solubility. A suitable hydroxyaromatic compound may be a phenol. In accordance with the present disclosure, the hydroxyaromatic compound may be substituted with at least one substituent other than the hydroxyl moiety. For example, at least one substituent may be chosen from alkyl and alkenyl moieties, such as C1-C4 alkyl and alkenyl moieties. Representative examples of hydroxyaromatic compounds useful in the process disclosed herein include phenolic compounds, including alkyl-substituted phenols. Phenolic compounds that may be used include high molecular weight alkyl-substituted derivatives of resorcinol, hydroquinone, cresol, catechol, xylenol, hydroxydiphenyl, benzylphenol, phenethylphenol, naphthol, and tolylnaphthol, among others, all of which may be optionally further substituted with any other substituent. The other substituent may be chosen from, for example, halogen, hydroxyl, alkyl, alkenyl, alkynyl, nitro, and amino radicals. Additional non-limiting examples of suitable oxyaromatic compounds include 4-octylphenol, 4-heptylphenol, 4-nonylphenol, and 4-dodecylphenol.

Mention may also be made of polypropylphenol (formed by alkylating phenol with polypropylene), polybutylphenols (formed by alkylating phenol with polybutenes and/or polyisobutylene), and polybutyl-co-polypropylphenols (formed by alkylating phenol with a copolymer of butylene and/or butylene and propylene). Other similar long-chain alkylphenols may also be used. Examples include phenols alkylated with copolymers of butylene and/or isobutylene and/or propylene, and one or more mono-olefinic comonomers copolymerizable therewith (e.g., ethylene, 1-pentene, 1-hexene, 1-octene, 1-decene, etc.) where the copolymer molecule contains at least 50% by weight of butylene and/or isobutylene and/or propylene units. Such compounds may be further substituted with at least one additional group, e.g., alkyl groups, for example $C_1$-$C_4$ alkyl groups, such as methyl. According to one aspect of the present disclosure, a suitable hydroxyaromatic compound may be polyisobutylcresol. The comonomers polymerized with propylene or the butylenes may be aliphatic and can also contain non aliphatic groups, e.g., styrene, o-methylstyrene, p-methylstyrene, divinyl benzene, and the like. Thus, in any case the resulting polymers and copolymers used in forming the alkyl-substituted hydroxyaromatic compounds may be substantially aliphatic hydrocarbon polymers.

Polybutylphenol (formed by alkylating phenol with polybutylene) may be suitable for the purposes of the present disclosure. The polybutylphenol ring may be further substituted with, for example, alkyl groups, such as lower, e.g., $C_1$-$C_4$, alkyl groups, for example methyl, in addition to other groups such as, for example, halogen, hydroxyl, alkyl, alkenyl, alkynyl, nitro, and amino radicals.

According to one aspect of the present disclosure, the polybutylphenol may be polyisobutylcresol. Unless otherwise specified herein, the term "polybutylene" is used in a generic sense to include polymers made from "pure" or "substantially pure" 1-butene or isobutene, and polymers made from mixtures of two or all three of 1-butene, 2-butene and isobutene. Commercial grades of such polymers may also contain insignificant amounts of other olefins. So-called high reactivity polybutylenes having relatively high proportions of polymer molecules having a terminal vinylidene group, formed by methods such as described, for example, in U.S. Pat. No. 4,152,499, and W. German Offenlegungsschrift 29 04 314, which may also be suitable for use in forming the long chain alkylated phenol reactant.

The alkylation of the hydroxyaromatic compound may be performed in the presence of an alkylating catalyst at a temperature ranging from about 50 to about 200° C. Acidic catalysts may generally be used to promote Friedel-Crafts alkylation. Typical catalysts used in commercial production include, but are not limited to, sulfuric acid, $BF_3$, aluminum-phenoxide, methane-sulfonic acid, cationic exchange resin, acidic clays, and modified zeolites.

The long chain alkyl substituents on the benzene ring of the phenolic compound may be derived from polyolefins having a number average molecular weight of from about 500 to about 3000 (for example, from about 500 to about 2000) as determined by gel permeation chromatography (GPC). The polyolefin may also have a polydispersity (weight average molecular weight/number average molecular weight) in the range of about 1 to about 4, for example from about 1 to about 2, as determined by GPC.

According to certain aspects of the present disclosure, polyalkylphenol reactants, e.g., polypropylphenol and polybutylphenol whose alkyl groups have a number average molecular weight of from 650 to 1200 may be suitable for the preparation of the Mannich base. According to certain embodiments, an alkyl group useful in accordance with the present disclosure may be a polybutyl group derived from polybutylene having a number average molecular weight in the range of from 650 to 950.

According to certain aspects of the present disclosure, a suitable configuration of the alkyl-substituted hydroxyaromatic compound may be that of a para-substituted monoalkylphenol. However, any alkylphenol readily reactive with the optionally substituted aldehyde may be employed. Thus, amines made from hydroxyaromatic compounds having only one ring alkyl substituent, or at least two ring alkyl substituents may be suitable for use in accordance with the present disclosure. The long-chain alkyl substituents may contain some residual unsaturation, or may be substantially saturated alkyl groups. According to certain embodiments, the long chain alkyl groups may be partially unsaturated. According to one aspect of the disclosure, the long-chain alkyl groups may have a degree of unsaturation ranging from 5 to 80%, for example from 10 to 50%.

According to certain aspects of the present disclosure, the hydroxyaromatic compound may be an alkylated phenol, may be substituted in the para-position, may contain at least 8 carbon atoms, and may have a molecular weight ranging from 205 g/mol to 1000 g/mol. According to another aspect of the present disclosure, suitable non-limiting examples of the hydroxyaromatic compound include phenols alkylated in the para-position with polypropylene, e.g., polypropylenephenols having molecular weights ranging from 500 to 5000 g/mol, and phenols reacted in the para-position with a-olefins containing at least 8 carbons. Mixtures of such phenols may also be used. The phenol mixtures may also contain small levels of 2,4-alkylated phenols.

The aldehyde source useful for the purposes of the present disclosure may include any source capable of providing an aldehyde to participate in the Mannich reaction. The aldehyde source can be any aldehyde, for example those containing from 1 to 6 carbon atoms such as formaldehyde, acetaldehyde, propionaldehyde, butyraldehyde, valeraldehyde, hexyldehyde, and the like. Aldehydes suitable for the purposes of the present disclosure may include the low molecular weight aliphatic aldehydes containing from 1 to 4 carbon atoms such as formaldehyde, acetaldehyde, butyraldehyde, isobutyraldehyde, and the like. According to one aspect of the present disclosure, the aldehyde source may be a formaldehyde source. Suitable non-limiting examples of formaldehyde sources include formaldehyde, paraformaldehyde, and aqueous formaldehyde solutions, such as formalin. The formaldehyde may be inhibited or uninhibited, and may be in solution, for example aqueous or aqueous-alcoholic solution.

According to certain aspects of the disclosure, the aqueous-alcoholic solutions may be aqueous methanolic or ethanolic formaldehyde solutions, wherein the formaldehyde may be present as a 5 to 80% aqueous solution, containing 0.5 to 60% aqueous alcohol solution. Non-limiting examples of such solutions include 37% aqueous formaldehyde containing 1.5% methanol, 37% aqueous formaldehyde containing 15% methanol, 44% aqueous formaldehyde containing 70% methanol, and 44% aqueous formaldehyde containing 1% methanol.

The amines useful for the purposes of the present disclosure may include hydroxyethyl substituted diamines. Any compound containing at least two amino groups and a hydroxyethyl substituent may be useful according to certain aspects of the present disclosure. Suitable non-limiting examples of such amines include 2-(2-aminoethylamino) ethanol, aminopropyldiethanolamine, aminoethyldiethanolamine, N-hydroxyethyl-1,3-propanediamine, and combinations of any of the foregoing. According to certain aspects of the disclosure, an amine suitable for the purposes of the present disclosure may be 2-(2-aminoethylamino)ethanol.

The Mannich reaction may be performed in bulk (no diluent or solvent), or in a solvent or diluent. Suitable solvents or diluents may include those that are inert and/or may be easily removed if desired, such as organic solvents, for example aromatic solvents such as benzene, xylene, or toluene. The solvent, when used, may be present as, for example, 1 part hydroxyaromatic compound to 1 part solvent. Significantly lower levels of solvent may cause the reflux temperature to rise and result in a product that colors finished oils/lubricants. Significantly higher levels of solvent may require longer reaction times, and possibly cause the molybdenum incorporation to stall.

The molar ratio of the amine to the hydroxyaromatic compound may range from 1:3 to 3:1. According to certain aspects of the disclosure, the ratio may be 2:1. According to another aspect, the ratio of amine to hydroxyaromatic compound may be 1:1. The molar ratio of formaldehyde to amine may range from 1:2 to 2:1. According to certain aspects of the disclosure, the ratio ranges from 1:1 to 1.5:1.

According to certain aspects of the disclosure, the amine, formaldehyde source, hydroxyaromatic compound, and solvent may be combined and heated to reflux temperature under nitrogen as water generated by the reaction is removed azeotropically. The reaction temperature may be determined by the reflux temperature of the water/solvent azeotrope, which in the case of toluene starts at approximately 84° C. and rises as water is removed from the reaction. The final reaction temperature varies depending on the amount of solvent, such as toluene, used in the reaction, and may range from 120° C. to 150° C. The reaction may take 1 to 3 hours for complete removal and formation of the Mannich product. The completed reaction may be cooled to approximately 60° C. in preparation for the molybdenum incorporation step.

II. Incorporation of Molybdenum

A molybdenum source useful for the purposes of the present disclosure includes any source that provides available molybdenum capable of reacting with a Mannich base. According to certain aspects of the disclosure, a suitable molybdenum source may be a molybdenum oxide. A suitable, non-limiting example of a molybdenum oxide useful for the purposes of the present disclosure may be molybdenum trioxide. The use of molybdenum trioxide may result in effective molybdenum incorporation into an organic ligand. Any purity grade of molybdenum trioxide may be used, but high purity molybdenum trioxide may be more likely to produce a product that does not require filtration.

A source of molybdenum, for example molybdenum trioxide, and water may be added to the Mannich reaction mass maintained at approximately 60° C. The molybdenum trioxide may be reacted with the Mannich base at a molar ratio of 2:1 to 1:3. According to certain aspects of the disclosure, the ratio may be 1:2. According to another aspect of the disclosure, the ratio may be 1:1. The amount of water used may generally be equivalent to the amount of molybdenumtrioxide used, but higher levels of water may also be used.

After addition of molybdenum trioxide and water, the reaction may be slowly heated to reflux temperature with gradual removal of water by azeotropic distillation. The reaction can be monitored by removal of water. The amount of water collected may be equal to the amount added plus the amount generated to produce the organic molybdenum complex. For example, if 14.4 g of molybdenum trioxide is used and 14.4 g of water is used, the amount of water collected may be 14.4+14:4/143.94×18.01=16.2 g, where 143.94 is the molecular weight of molybdenum trioxide and 18.01 is the molecular weight of the water generated in the reaction. The reaction may require anywhere from 2 to 8 hours. The reaction mass may be cooled, may be filtered to remove any unreacted molybdenum trioxide, and the toluene, may be removed by vacuum distillation. The product prepared by this process may be a dark red, highly viscous liquid.

III. Formulations

The organic molybdenum complex containing compositions of the present disclosure may be useful to improve at least one of deposit control, antioxidant, antiwear, and/or friction modifying properties of lubricant oils, and like materials. The inclusion of the present organic molybdenum complexes may generally remove the need for supplementary deposit control or antioxidants, antiwear additives and the like. However, a supplementary deposit control, antioxidant, and/or antiwear additive may be included in the finished oils/lubricants including the molybdenum additives of the present disclosure that are less oxidatively stable, or in oils that are subjected to unusually severe conditions. The treat rates of the molybdenum additives may depend upon the desired finished oil/lubricant properties; however, typically the additives may be present in an amount so as to provide at least about 50, and for example from about 50 to about 1000 ppm, of molybdenum to the finished product. The concentration of molybdenum in the lubricants according to the present disclosure has no particular upper limit; however, for economic reasons a maximum level of about 1000 ppm may generally be used, although not required.

The treat rates of the organic molybdenum complexes according to the present disclosure may depend upon the desired finished lubricant properties; however, typically the additives may be present in an amount so as to provide at least about 50 ppm, for example from about 50 to about 1000 ppm, of molybdenum to the finished lubricant. The concentration of molybdenum in the lubricants according to the invention has no particular upper limit; however, for economic reasons a maximum level of about 1000 ppm may generally be employed, although not required. The table below summarizes exemplary, non-limiting treat rates and additive combinations for various applications:

| Application | Suitable Treat Range | Performance Boosting Additives | Oil Type |
|---|---|---|---|
| Antioxidant | 75-250 ppm Mo | Diphenylamines (0.05-1.0%) Sulfur-Containing Additives (0.2-1%), Sulfurized Phenate Detergents (0.3-3.0%) ZDDP (0.5-1.2%) | Passenger Car and Medium Speed Diesel Oils |
| Anti-Wear | 50-100 ppm Mo | ZDDP Sulfur-Containing Additives | Passenger Car and Heavy Duty Diesel Oils |
| Deposit Control | 75-250 ppm Mo | Diphenylamines (0.05-1.0%) Sulfurized Phenate Detergents (0.2-3.0%) | Heavy Duty Diesel and Natural Gas Engine Oils |
| Friction Modifying | 250-1000 pm Mo | Antioxidants (0.1-1.0%) | Passenger Car Oils |

The organic molybdenum complexes of the present disclosure may have excellent solubility in a wide variety of basestock types and/or may have a reduced tendency to color finished crankcase oils. Further, the complexes may be capable of high molybdenum incorporations, may be prepared from low cost raw materials, and/or may have straightforward production processes.

The composition of the lubricant oil may vary significantly based on the customer and specific application. The oil may typically contain, in addition to the molybdenum compounds of the present disclosure, a detergent/inhibitor additive package and a viscosity index improver. In general, the lubricant oil may be a formulated oil which may be composed of from about 65 to 95 weight percent (wt. %) of a base oil of lubricating viscosity, from about 0 to 30 wt. % of a polymeric viscosity index improver, from about 5 to 15 wt. % of an additional additive package and typically a sufficient amount of organic molybdenum complex to provide at least about 50 ppm of molybdenum to the finished lubricant.

The detergent inhibitor additive package may include at least one of dispersants, detergents, zinc dihydrocarbyl dithiophosphates (ZDDP), additional antioxidants, pourpoint depressants, corrosion inhibitors, rust inhibitors, foam inhibitors and supplemental friction modifiers.

The dispersants may be, according to certain aspects of the present disclosure, nonmetallic additives containing nitrogen or oxygen polar groups attached to a high molecular weight hydrocarbon chain. The hydrocarbon chain may provide solubility in the hydrocarbon base stocks. The dispersant may function to keep oil degradation products suspended in the oil. Suitable non-limiting examples of commonly used dispersants include hydrocarbyl-substituted succinimides, hydrocarbyl amines polyhydroxy succinic esters, hydrocarbyl-substituted Mannich bases, and hydrocarbyl-substituted triazoles. Generally, the dispersant may be present in the finished oil in an amount ranging from 0 to 10 wt. %.

The detergents may be chosen from metallic additives containing charged polar groups, such as phenates, sulfonates or carboxylates, with aliphatic, cycloaliphatic, or alkylaromatic chains, and several metal ions. The detergents may function by lifting deposits from the various surfaces of the engine. Suitable, non-limiting examples of commonly used detergents include neutral and overbased alkali and alkaline earth metal sulfonates, overbased alkaline earth salicylates, phosphonates, thiopyrophosphonates, and thiophosphonates. Generally, when used, the detergents may be present in the finished oil in an amount ranging from 0.5 to 5.0 wt. %.

The ZDDP's are the most commonly used antiwear additives in formulated lubricants. These additives may function by reacting with the metal surface to form a new surface active compound which itself may be deformed and thus may protect the original engine surface". Other examples of suitable anti-wear additives include tricresol phosphate, dilauryl phosphate, sulfurized terpenes and sulfurized fats. The ZDDP also may function as an antioxidant. Generally, the ZDDP may be present in the finished oil in an amount ranging from 0.25 to 1.5 wt. %. It may be desirable, due to environmental concerns, to use lower levels of ZDDP. Phosphorus-free oils contain no ZDDP.

The inclusion of the present molybdenum compounds may generally remove the need for supplemental antioxidants. However, a supplementary antioxidant may be included in oils that are less oxidatively stable, or in oils that are subjected to unusually severe conditions. The amount of supplemental antioxidant may vary depending on the oxidative stability of the base stock. Typical treat levels in finished oils can vary from 0 to 2.5 wt %. The supplementary antioxidants that may generally be used include diarylamines, hindered phenols, hindered bisphenols, sulfurized phenols, sulfurized olefins, alkyl sulfides and polysulfides, dialkyl dithiocarbamates, and phenothiazines.

The base oil according to the present disclosure may be selected from any of the synthetic or natural oils or mixtures thereof. These oils may be typical crankcase lubrication oils for spark-ignited and compression-ignited internal combustion engines, for example natural gas engines, automobile and truck engines, marine, and railroad diesel engines. The synthetic base oils include alkyl esters of dicarboxylic acids, polyglycols and alcohols, poly-alpha-olefins, including polybutenes, alkyl benzenes, organic esters of phosphoric acids, and polysilicone oils. Natural base oils include mineral lubrication oils that may vary widely as to their crude source, e.g., as to whether they are paraffinic, naphthenic, or mixed paraffinicnaphthenic. The base oil typically has a viscosity ranging from 2 to about 15 cSt, for example from 2.5 to 11 cSt at 100° C.

The lubricating oil compositions according to the present disclosure can be made by adding the molybdenum compound, and any supplemental additives, to an oil of lubricating viscosity. The method or order of component addition is not critical. The molybdenum compounds, along with any additional additives, can be added to the oil as a concentrate.

The lubricating oil concentrate may typically comprise a solvent and from 2.5 to 90 wt. %, for example 5 to 75 wt. % of the combination of the organic molybdenum complex of the present disclosure and the optional supplemental additives. According to certain aspects of the present disclosure, the concentrate comprises at least 25 wt. %, for example at least 50 wt. % of the combination of organic molybdenum complex and supplemental additives.

IV. Preparatory Examples

EXAMPLE 1

A. Stage 1

52.5 g (0.2 mol) of 4-dodecylphenol, 20.8 g (0.2 mol) of 2-(2-aminoethylamino)ethanol, 7.9 g of paraformaldehyde and 43 g of xylenes were charged to a reaction flask equipped with a stirrer, a Dean-Stark trap, and a heating mantle. The stirred reaction mixture was heated to reflux and water was removed azeotropically. The Mannich reaction product was cooled to about 60° C.

B. Stage 2

To the Mannich reaction product at 60° C. was added 14.4 g (0.1 mol) of molybdenum (VI) oxide and 15 mL of deionized water. The reaction mixture was gradually heated to reflux with azeotropic removal of water. After 3 hours at reflux, the reaction mixture was diluted with 100 g of process oil #5 and filtered The filtrate was concentrated in vacuo to afford 188.9 g of product.

EXAMPLE 2

A. Stage 1

211 g (0.8 mol) of 4-dodecylphenol, 83.6 g (0.8 mol) of 2-(2-aminoethylamino)ethanol, 67.4 mL of 37% formaldehyde solution and 260 mL of toluene were charged to a reaction flask equipped with a stirrer, a Dean-Stark trap, and a heating mantle. The stirred reaction mixture was heated at reflux for 2 hours and water was removed azeotropically. The Mannich reaction product was cooled to about 60° C.

B. Stage 2

To the Mannich reaction product at 60° C. was added 64 g (0.44 mol) of molybdenum (VI) oxide and 120 mL of deionized water. The reaction mixture Was gradually heated to reflux with azeotropic removal of water. After 6 hours at reflux, the reaction mixture Was diluted with 380 g of process oil #5 and filtered and concentrated in vacuo to afford 740.2 g of product.

COMPARATIVE EXAMPLE A

A. Stage 1

52.5 g (0.2 mol) of 4-dodecylphenol, 60 g of Duomeen T, 6.3 g of paraformaldehyde, and 50 mL of toluene were charged to a reaction flask equipped with a stirrer, a Dean-Stark trap, and a heating mantle. The stirred reaction mixture was heated to reflux and water was removed azeotropically. The Mannich reaction product was cooled to about 60° C.

B. Stage 2

To the Mannich reaction product at 60° C. was added 14.4 g 0.1 mmol) of molybdenum (VI) oxide and 15 mL of deionized water. The reaction mixture was gradually heated to reflux with azeotropic removal of water. After 3 hours at reflux the reaction mixture was diluted with 50 g of process oil #5 and filtered. The filtrate was concentrated in vacuo to afford 177.5 g of product.

COMPARATIVE EXAMPLE B

A. Stage 1

52.5 g (0.2 mol) of 4-dodecylphenol, 6 g (0.2 mol) of ethylenediamine, 6.3 g of paraformaldehyde and 50 mL of toluene were charged to a reaction flask equipped with a stirrer, a Dean-Stark trap, and a heating mantle. The stirred reaction mixture was heated to reflux and water was removed azeotropically. The Mannich reaction product was cooled to about 60° C.

B. Stage 2

To the Mannich reaction product at 60° C. was added 7.2 g (0.05 mol) of molybdenum (VI) oxide and 7.5 mL of deionized water. The reaction mixture was gradually heated to reflux with azeotropic removal of water. After 3 hours at reflux, the reaction mixture was diluted with 50 g of process oil #5 and filtered. The filtrate was concentrated in vacuo to afford 166.8.5 g of product

COMPARATIVE EXAMPLE C

A. Stage 1

52.5 g (0.2 mol) of 4-dodecylphenol, 10.3 g (0.1 mol) of diethylenetriamine, 6.3 g of paraformaldehyde, and 50 mL of toluene were charged to a reaction flask equipped with a stirrer, a Dean-Stark trap, and a heating mantle. The stirred reaction mixture was heated to reflux and water was removed azeotropically. The Mannich reaction product was cooled to about 60° C.

B. Stage 2

To the Mannich reaction product at 60° C. was added 14.4 g (0.1 mol) of molybdenum (VI) oxide and 15 mL of deionized water. The reaction mixture was gradually heated to reflux with azeotropic removal of water. After 3 hours at reflux, the reaction mixture was diluted with 50 g of process oil #5 and filtered. The filtrate was concentrated in vacuo to afford 176.3 g of product.

The efficacy of friction modifiers in lubricating oils can be determined by measuring the boundary friction coefficient in a high frequency reciprocating rig (HFRR). Effective friction modifiers lower the lubricant's boundary friction coefficient.

Figure 1:
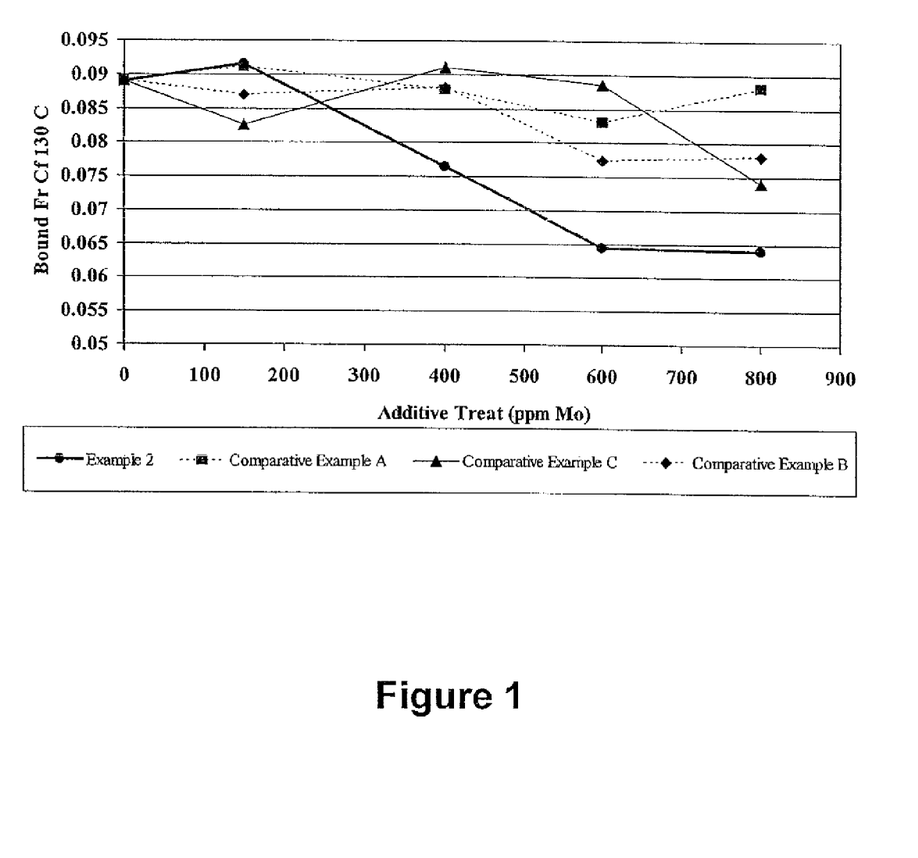
FIG. 1 illustrates the boundary friction coefficients of finished oils containing molybdenum additives.

Example 2 and comparative examples A, B and C were blended into a SAE 5W-30 GF-3 type formulation to deliver 100, 400, 600 and 800 ppm Mo in the finished oil. FIG. 1 illustrates the boundary friction coefficients at these treat rates. Example 2 was significantly more effective at reducing the boundary friction coefficient than any of the molybdenum-containing comparative examples.

Figure 2:
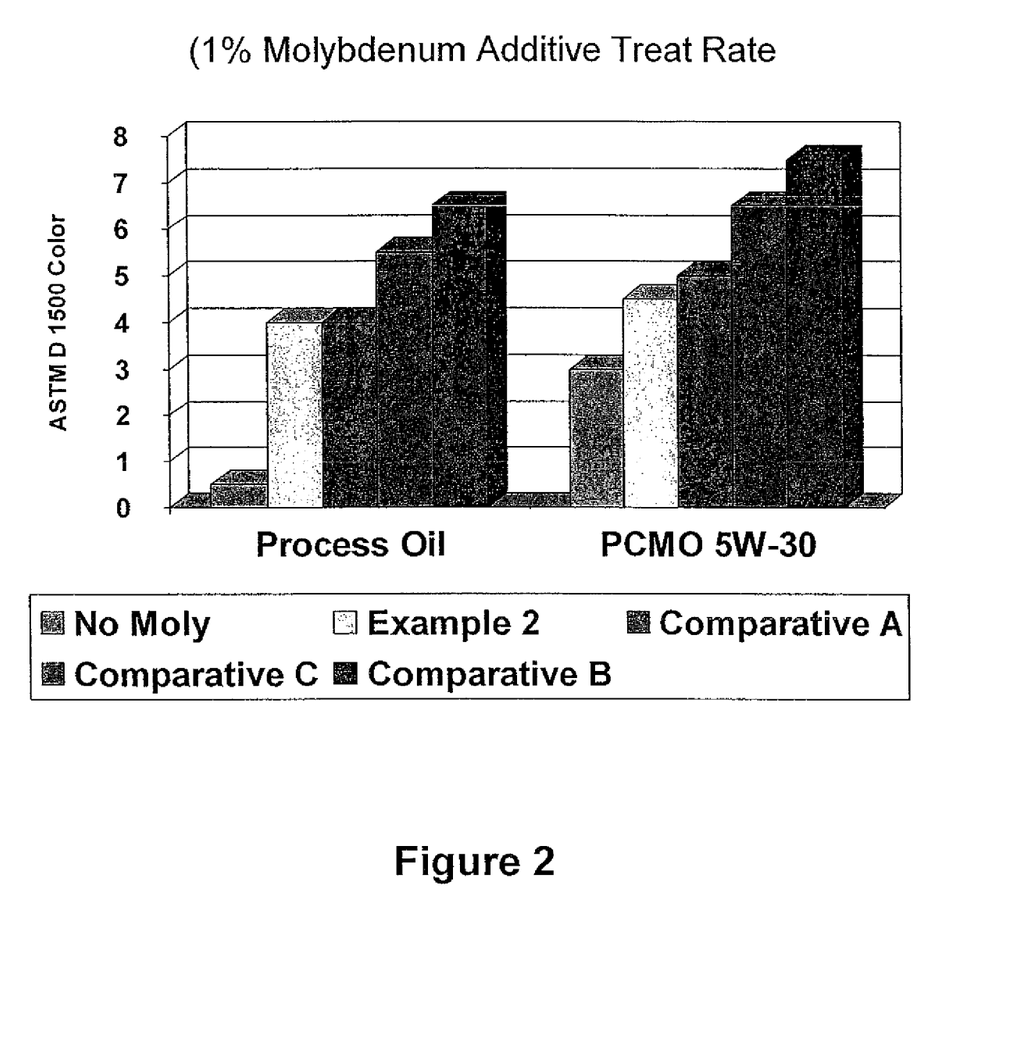
FIG. 2 illustrates color formation in various oils containing molybdenum compounds.

Many molybdenum additives can darken the color of lubricant oils. Dark lubricant oil due to the contribution of molybdenum additives is purely an aesthetic issue, and not a performance issue. The ASTM D 1500 color scale was used to determine the effects of Example 2 and comparative examples A, Band, C. These molybdenum additives were blended at 1% treat rate in a SAE 5W-30 formulation and in process oil #5. FIG. 2 illustrates the results of the ASTM D 1500 color test. Example 2 and comparative example A produced the lightest oils in color relative to the other comparative examples. Example 2 produced lighter oil than comparative example A when blended in the SAE 5W-30 lubricant.

Other embodiments of the invention will be apparent to those skilled in the art from consideration of the specification and practice of the invention disclosed herein. It is intended that the specification and examples be considered as exemplary only, I with a true scope and spirit of the invention being indicated by the following claims.

What is claimed is:

1. A lubricating oil composition comprising a major amount of an oil of lubricating viscosity and an organic molybdenum complex prepared by a process comprising:
   (a) reacting an alkylphenol substituted with an alkyl group in the para-position with a formaldehyde source and an N-hydroxyethyl substituted diamine to yield a Mannich base; and
   (b) reacting the Mannich base with molybdenum trioxide to form the organic molybdenum complex,
   wherein the N-hydroxyethyl substituted diamine is selected from the group consisting of 2-(2-aminoethylamino)ethanol, aminopropyldiethanolamine, and aminoethyldiethanolamine.

2. The lubricating oil composition according to claim 1, wherein the organic molybdenum complex is oil-soluble.

3. A lubricating composition comprising an organic molybdenum complex comprising the reaction product of:
   (i) an alkylphenol substituted with an alkyl group in the para-position;
   (ii) an aldehyde source;
   (iii) an N-hydroxyethyl substituted diamine selected from the group consisting of 2-(2-aminoethylamino)ethanol, aminopropyldiethanolamine, and aminoethyldiethanolamine; and
   (iv) molybdenum trioxide.

4. An antioxidant composition comprising an organic molybdenum complex comprising the reaction product of:
   (i) an alkylphenol substituted with an alkyl group in the para-position;
   (ii) an aldehyde source;
   (iii) an N-hydroxyethyl substituted diamine selected from the group consisting of 2-(2-aminoethylamino)ethanol, aminopropyldiethanolamine, and aminoethyldiethanolamine; and
   (iv) molybdenum trioxide.

5. The antioxidant composition according to claim 4, wherein the organic molybdenum complex is present in the composition in an amount sufficient to provide molybdenum in an amount ranging from 75 to 250 ppm.

6. The antioxidant composition according to claim 4, further comprising at least one of diphenylamines, sulfur-containing additives, sulfurized phenate detergents, and ZDDP.

7. An anti-wear composition comprising an organic molybdenum complex comprising the reaction product of:

(i) an alkylphenol substituted with an alkyl group in the para-position;
(ii) an aldehyde source;
(iii) an N-hydroxyethyl substituted diamine selected from the group consisting of 2-(2-aminoethylamino)ethanol, aminopropyldiethanolamine, and aminoethyldiethanolamine; and
(iv) molybdenum trioxide.

8. The anti-wear composition according to claim 7, wherein the organic molybdenum complex is present in the composition in an amount sufficient to provide molybdenum in an amount ranging from 50 to 100 ppm.

9. The anti-wear composition according to claim 7, further comprising at least one of sulfur-containing additives and ZDDP.

10. A deposit control composition comprising an organic molybdenum complex comprising the reaction product of:
(i) an alkylphenol substituted with an alkyl group in the para-position;
(ii) an aldehyde source;
(iii) an N-hydroxyethyl substituted diamine selected from the group consisting of 2-(2-aminoethylamino)ethanol, aminopropyldiethanolamine, and aminoethyldiethanolamine; and
(iv) molybdenum trioxide.

11. The deposit control composition according to claim 10, wherein the organic molybdenum complex is present in the composition in an amount sufficient to provide molybdenum in an amount ranging from 75 to 250 ppm.

12. The deposit control composition according to claim 10, further comprising at least one of diphenylamines and sulfurized phenate detergents.

13. A friction modifying composition comprising an organic molybdenum complex comprising the reaction product of:
(i) an alkylphenol substituted with an alkyl group in the para-position;
(ii) an aldehyde source;
(iii) an N-hydroxyethyl substituted diamine selected from the group consisting of 2-(2-aminoethylamino)ethanol, aminopropyldiethanolamine, and aminoethyldiethanolamine; and
(iv) molybdenum trioxide.

14. The friction modifying composition according to claim 13, wherein the organic molybdenum complex is present in the composition in an amount sufficient to provide molybdenum in an amount ranging from 250 to 1000 ppm.

15. The friction modifying composition according to claim 13, further comprising an antioxidant.

16. An additive concentrate composition comprising:
a) an organic molybdenum complex comprising the reaction product of:
(i) an alkylphenol substituted with an alkyl group in the para-position;
(ii) an aldehyde source;
(iii) an N-hydroxyethyl substituted diamine selected from the group consisting of 2-(2-aminoethylamino)ethanol, aminopropyldiethanolamine, and aminoethyldiethanolamine; and
(iv) molybdenum trioxide; and
b) a diluent process oil.

17. The additive concentrate composition according to claim 16, further comprising at least one additive chosen from dispersants, detergents, anti-wear agents, anti-oxidants, viscosity index improvers, pour point depressants, corrosion inhibitors, rust inhibitors, foam inhibitors, and friction modifiers.

18. A process for reducing the oxidative environment in a lubricating oil composition, the process comprising combining with the lubricating oil composition an effective amount of the antioxidant composition according to claim 4.

19. A process for lubricating a crankcase, comprising adding a lubricating oil composition according to claim 1 to a crankcase.

20. A crankcase lubricated with a composition according to lubricating oil composition according to claim 1.

21. A process for improving the oxidation stability of a lubricating oil comprising adding to the lubricating oil an oxidation stability improving amount of an organic molybdenum complex comprising the reaction product of:
(i) an alkylphenol substituted with an alkyl group in the para-position;
(ii) an aldehyde source;
(iii) an N-hydroxyethyl substituted diamine selected from the group consisting of 2-(2-aminoethylamino)ethanol, aminopropyldiethanolamine, and aminoethyldiethanolamine; and
(iv) molybdenum trioxide,
wherein the oxidation stability improving amount of the molybdenum complex is sufficient to improve the oxidative stability of the lubricating oil, as compared to the same lubricating oil except that it is devoid of the organic molybdenum complex.

22. The process according to claim 21, wherein the organic molybdenum complex is present in the lubricating oil in an amount sufficient to provide at least 50 ppm of molybdenum to the finished lubricating oil.

23. A process for improving the fuel economy of an internal combustion engine comprising using as a crankcase lubricating oil for the internal combustion engine the lubricating oil composition of claim 1, wherein the organic molybdenum complex is present in an amount sufficient to improve the fuel economy of the internal combustion engine using the crankcase lubricating oil composition, as compared to the engine operated in the same manner and using the same crankcase lubricating oil except that the oil is devoid of the organic molybdenum complex.

24. The process according to claim 23, wherein the organic molybdenum complex is present in the crankcase lubricating oil in an amount sufficient to provide at least 50 ppm of molybdenum to the finished lubricating oil.

25. A process for reducing deposits in an internal combustion engine comprising using as a crankcase lubricating oil for the internal combustion engine the lubricating oil composition of claim 1, wherein the organic molybdenum complex is present in an amount sufficient to reduce the weight of deposits in an internal combustion engine operated using the crankcase lubricating oil, as compared to the weight of deposits in the engine operated in the same manner and using the same crankcase lubricating oil except that the oil is devoid of the organic molybdenum complex.

26. The process according to claim 25, wherein the organic molybdenum complex is present in the crankcase lubricating oil in an amount sufficient to provide at least 50 ppm of molybdenum to the finished lubricating oil.

27. A process for reducing wear in an internal combustion engine comprising using as a crankcase lubricating oil for the internal combustion engine the lubricating oil composition of claim 1, wherein the organic molybdenum complex is present in an amount sufficient to reduce the wear in an internal combustion engine operated using the crankcase lubricating oil, as compared to the wear in the engine operated in the same manner and using the same crankcase lubricating oil except that the oil is devoid of the organic molybdenum complex.

28. The process according to claim 27, wherein the organic molybdenum complex is present in the crankcase lubricating oil in an amount sufficient to provide at least 50 ppm of molybdenum to the finished lubricating oil.

29. A process for providing friction modification in an internal combustion engine comprising using as a crankcase lubricating oil for the internal combustion engine the lubricating oil composition of claim 1, wherein the organic molybdenum complex is present in an amount sufficient to reduce the wear in an internal combustion engine operated using the crankcase lubricating oil, as compared to the wear in the engine operated in the same manner and using the same crankcase lubricating oil except that the oil is devoid of the organic molybdenum complex.

30. The process according to claim 29, wherein the organic molybdenum complex is present in the crankcase lubricating oil in an amount sufficient to provide at least 50 ppm of molybdenum to the finished lubricating oil.

\* \* \* \* \*